United States Patent
Glukhov et al.

[11] Patent Number: 5,928,187
[45] Date of Patent: Jul. 27, 1999

[54] DEVICE FOR OXYGEN PROPHYLAXIS AND TREATMENT OF GUM DISEASES

[76] Inventors: Semyon A. Glukhov, 5022 Fulton Ave., Sherman Oaks, Calif. 91423; Serguei N. Efouni, 110-20 71 St. Rd., Apt. 608, Forest Mills, N.Y. 11375

[21] Appl. No.: 09/055,450

[22] Filed: Apr. 6, 1998

[51] Int. Cl.⁶ .......................... A61M 37/00; A61C 5/00; A61C 15/00
[52] U.S. Cl. .............. 604/23; 604/73; 433/215; 601/164
[58] Field of Search ...................... 601/139, 160, 601/162, 164, 165; 607/134; 600/239; 128/861, 207.14, 207.15, 207.16, 207.17, 201.11; D24/110.5, 110.6; 433/37, 80, 81, 84, 88, 215, 229; 604/890.1, 19, 23–27, 30, 35, 48, 54, 73, 77, 79, 93, 118, 247, 328

[56] References Cited

U.S. PATENT DOCUMENTS

| 803,475 | 10/1905 | Dennis . | |
|---|---|---|---|
| 3,060,935 | 10/1962 | Riddell | 604/54 |
| 4,116,239 | 9/1978 | Ewen | 128/184 |
| 4,243,155 | 1/1981 | Stewart | 222/3 |
| 4,560,351 | 12/1985 | Osborne | 433/80 |
| 4,624,656 | 11/1986 | Clark et al. | 604/23 |
| 4,664,109 | 5/1987 | Rasocha | 128/207.14 |
| 5,031,611 | 7/1991 | Moles | 128/201.11 |
| 5,104,315 | 4/1992 | McKinley | 433/80 |
| 5,203,324 | 4/1993 | Kinkade | 128/201.11 |
| 5,296,216 | 3/1994 | Turner | 424/53 |
| 5,327,218 | 7/1994 | Westline | 128/229 |
| 5,509,801 | 4/1996 | Nicholson | 433/80 |
| 5,755,224 | 5/1998 | Good et al. | 128/205.24 |
| 5,800,367 | 9/1998 | Saxer et al. | 601/164 |

FOREIGN PATENT DOCUMENTS 1052060   3/1959   Germany ............................ 604/77

*Primary Examiner*—Wynn Wood Coggins
*Assistant Examiner*—Sharon Finkel
*Attorney, Agent, or Firm*—Ilya Zborovsky

[57] ABSTRACT

A device for oxygen prophylaxis and treatment has a barochamber formed as a body having at least one groove for receiving a part of a gum and teeth in the gum in the groove in a sealed manner, and passage a unit for supplying oxygen from an oxygen source into the groove so as to provide prophylaxis and treatment of the gum and the teeth.

10 Claims, 3 Drawing Sheets

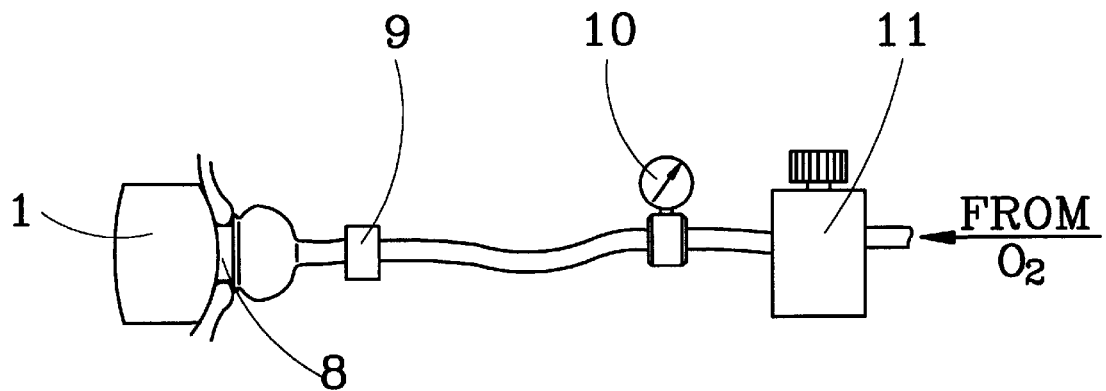
FIG.2
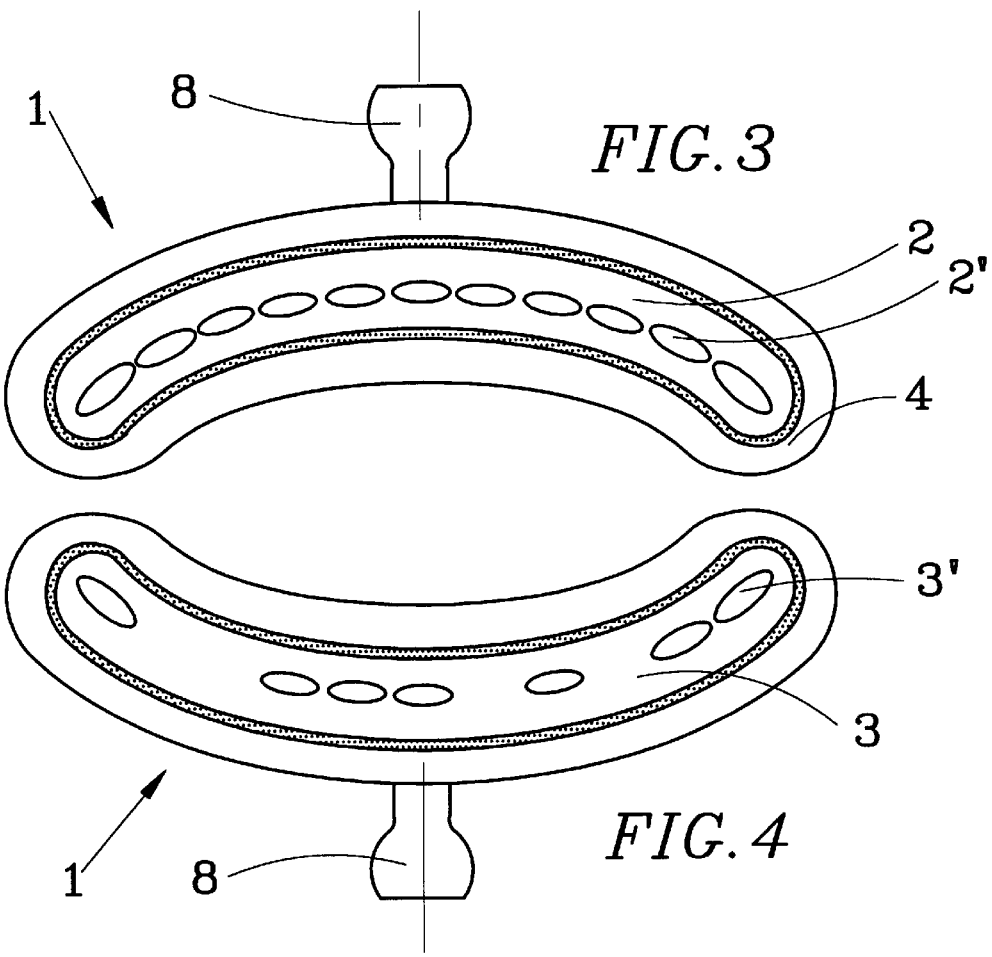
FIG.3
FIG.4

DEVICE FOR OXYGEN PROPHYLAXIS AND TREATMENT OF GUM DISEASES

BACKGROUND OF THE INVENTION

The present invention relates to a device for prophylaxis and treatment of gum diseases with the use of oxygen.

Devices for use of oxygen for treatment of gum disease, for example, paradonthosis are known. For example U.S. Pat. No. 4,116,239 discloses a device for supplying an oxygen stream onto the gum portion to be treated. The efficiency of treatment is not sufficient, since oxygen acts on soft tissues with atmospheric pressure, and its partial pressure remains less than 1 atm (or in other words below 14.7 psia or below 760 mm Hg), since at the last stage oxygen is mixed with air which is located around the part to be treated.

It is well known that in prophylaxis and treatment of diseases with direct outer action of oxygen onto soft tissues, it is especially efficient to use oxygen at increased pressure, which corresponds to increased partial pressure of oxygen. Under this condition the physical solubility of oxygen in soft tissues increases as well as its biological activity. For prophylaxis of gum diseases, it is especially important to act simultaneously on the whole surface of the upper and lower gums.

The use of hyperpar oxygen under high pressure in stomatology is well known. For example, the presentation of N. N. Bazhanov, et al "HYPERBARIC OXYGENATION IN COMPLEX TREATMENT OF STOMATOLOGICAL DISEASES", in this title of this article on VII International Congress of Hyperbaric Medicine presents data about the efficient use of barochamber, in which a patient with stomatological diseases is treated. However, such a device acts with elevated pressure of oxygen on all organs an organism as a whole, which is not always desirable, low efficient, and in some cases even dangerous.

SUMMARY OF THE INVENTION

Accordingly, it is an object of the present invention to provide a device for prophylaxis and treatment of gum diseases, which avoids the disadvantages of the prior art.

In keeping with these objects and with others which will become apparent hereinafter, one feature of present invention resides, briefly stated, in a device for prophylaxis and treatment of a gum diseases, comprising a barochamber forming means including a body provided with an open elongated groove formed so that at least teeth one gum and a portion of the gum with the teeth is insertable in the groove, and a passage communicating the groove with a source of oxygen under high pressure.

In accordance with another feature of present invention, the body can have two upper and lower grooves openly correspondingly upwardly and downwardly so that the teeth of the upper gum and the upper gum, as well as the teeth of the lower gum and the lower gum are insertable into the corresponding groove and oxygen is supplied into both grooves.

When the device is designed in accordance with present invention, it provides local prophylactic and treatment action exclusively on a gum (gums) and teeth under increased partial oxygen pressure.

The barochamber formed by the above mentioned body groove or grooves can be made for each patient individually with consideration of the profile of its gums and available teeth.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 2 is a schematic view showing the inventive device with additional elements;

FIGS. 3 and 4 are a top view and a bottom view of a main body of the inventive device;

DESCRIPTION OF PREFERRED EMBODIMENTS

Figure 1:
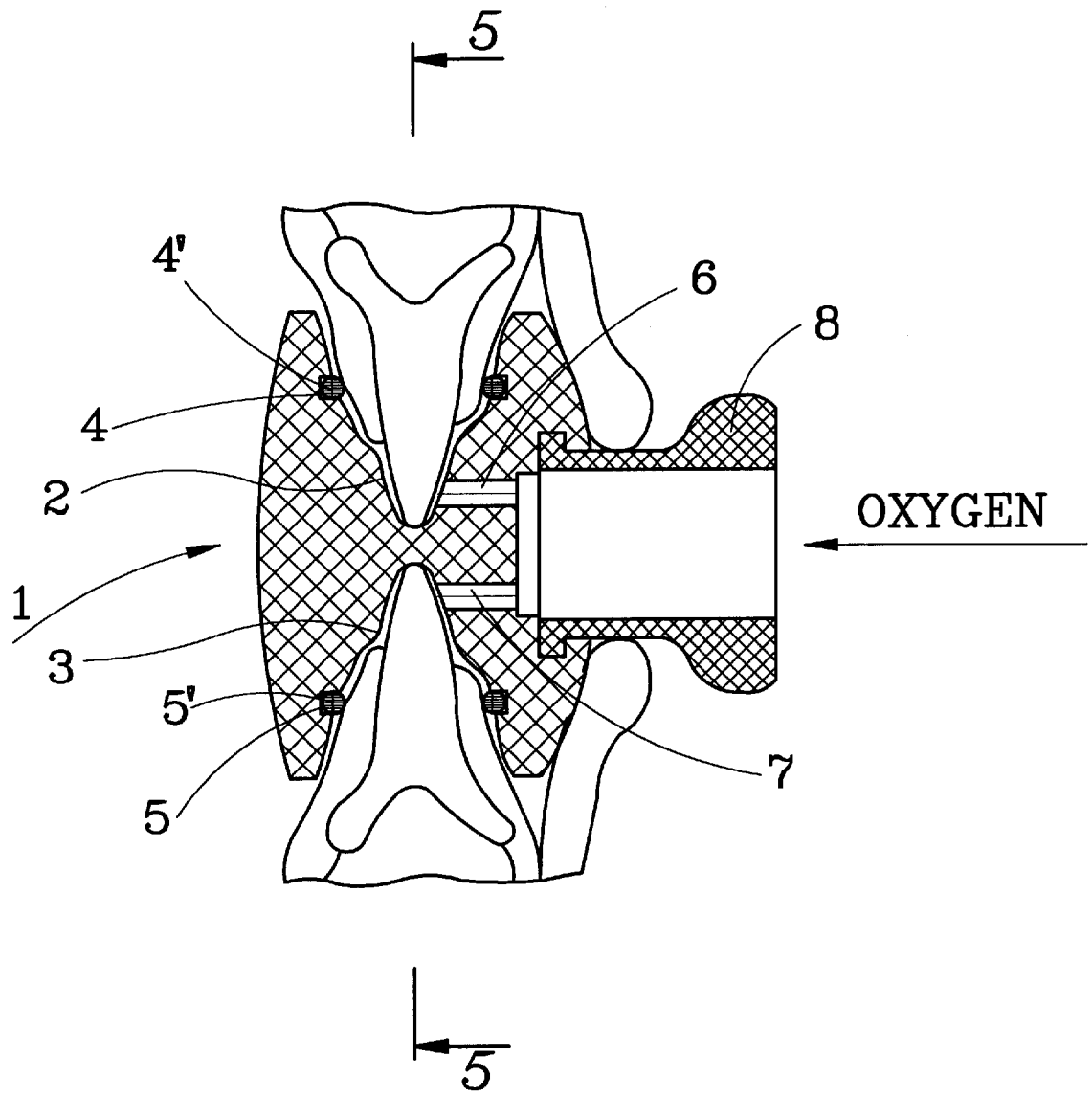
FIG. 1 is a view showing a cross-section of a device for prophylaxis and treatment of gum diseases in accordance with present invention.

A device for prophylaxis and treatment of gum diseases shown in FIG. 1 has a barochamber which is identified as a whole with reference numeral 1. A barochamber 1 is formed as a body including two grooves 2 and 3 provided in its upper region and lower region. The grooves 2 and 3 have a shape substantially corresponding to the shape of the upper gum with the upper teeth and the lower gum with the lower teeth correspondingly. While two grooves 2 and 3 are provided in the body for receiving both gums with both groups of teeth as shown in the drawings, only one groove can be provided for receiving of a portion of only one gum with its teeth. The body can be composed of rubber or soft plastic which can be made by molding in molds formed from actual imprints of the upper and lower teeth with portions of gum of a patient.

Sealing elements 4 and 5 can be provided in the grooves 2 and 3. The sealing elements can be formed as thin strips of soft material, such as rubber, attached to the lower surfaces of the grooves 2 and 3. On the other hand, the sealing elements can be formed as O-rings arranged in corresponding depressions 4' and 5' formed in the walls of the grooves 2 and 3.

The body is provided with passages 6 and 7 having one end open in the corresponding grooves 2 and 3 and another end communicating with an oxygen source for example through an adaptor or fitting 8.

As can be seen from FIG. 2, the adapter 8 is connected with an oxygen line formed for example as a hose. The oxygen line is provided with a relief valve 9, an oxygen pressure indicating element formed as a pressure gauge 10, and an oxygen pressure regulating element formed as a pressure flow regulator 11.

Figure 5:
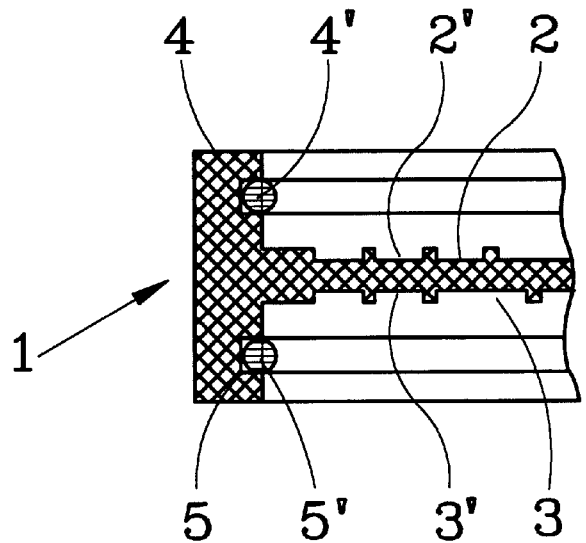
FIG. 5 is a section taken along the lines 5—5 in FIG. 1.

FIGS. 3, 4 and 5 disclose details of the body which forms the barochamber 1. As can be seen from FIGS. 3 and 4, the groove 2 and the groove 3 are composed of a plurality of individual depressions in which the individual teeth are inserted during the operation of the device.

Figure 6:
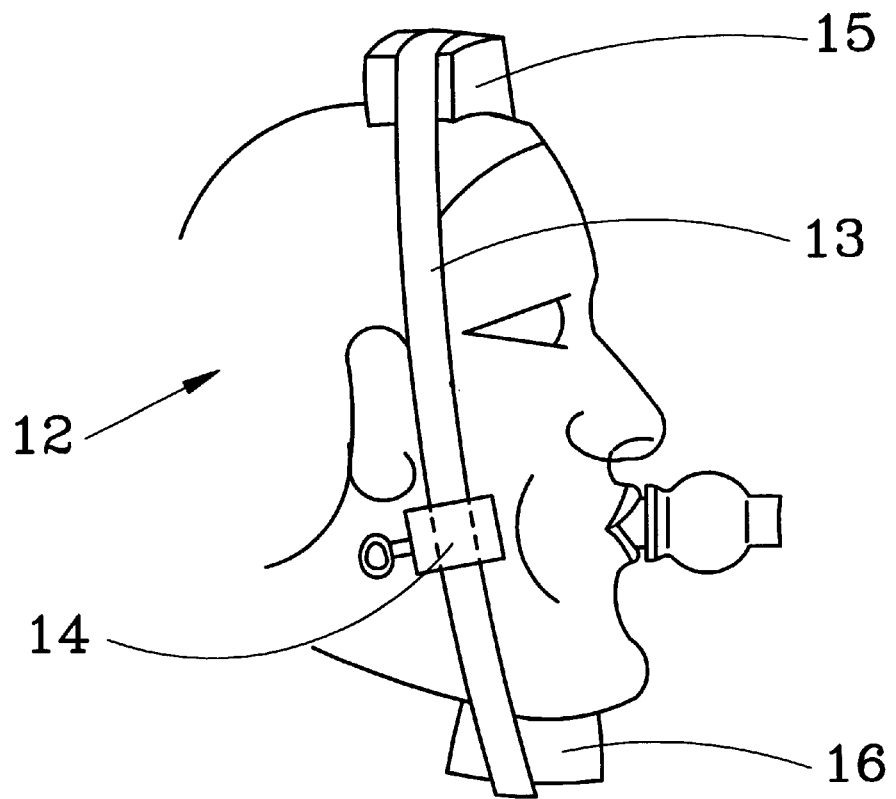
FIG. 6 is a view showing a head of a user with the inventive device and a head harness for holding together the upper and lower jaws.

As shown in FIG. 6, the device can have a holding unit which is identified as a whole with reference numeral 12. The holding unit includes a harness which includes a strap 13 is surrounding the user's head and provided with an adjusting element 14 for adjusting the length of the strap.

Upper 15 and lower 16 inserts can be arranged between the user's head and the strap 13 to tighten the straps so that the upper and lower gums are held together.

The inventive device for oxygen prophylaxis and treatment operates in the following manner.

The barochamber 1 is placed in a user's mouth so that his upper teeth with a portion of the upper gum and his lower teeth with a portion of the lower gum are introduced into the grooves 2 and 3. Then, the strap 13 is adjusted to hold the upper and lower gums together during the operation. Oxygen is supplied from the oxygen source at a high pressure through the passages 6 and 7 to the teeth and gums for oxygen prophylaxis and treatment. The pressure of oxygen can be identified by the pressure gauge 10 and regulated by the pressure flow regulator. To prevent excessive pressure and other risks, oxygen is relieved through the relief valve 9 when the oxygen pressure exceeds a predetermined value. During the prophylaxis or treatment, the sealing elements prevent oxygen escape and corresponding losses and assure the efficient treatment.

It will be understood that each of the elements described above, or two or more together, may also find a useful application in other types of constructions differing from the types described above.

While the invention has been illustrated and described as embodied in device for oxygen prophylaxis and treatment of gum diseases, it is not intended to be limited to the details shown since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for oxygen prophylaxis and treatment, comprising a body which forms a substantially closed barochamber having at least one groove formed as an actual imprint of teeth of at least one gum of a patient with a portion of the at least one gum, for receiving the teeth of the gum and the portion of the gum in said groove; means for sealing at least one groove so that the teeth of the gum and the portion of the gum are received in said groove in a sealed manner for preventing oxygen loss and increasing efficiency of oxygen treatment; and passage means for supplying oxygen from an oxygen source into said at least one groove so as to provide oxygen prophylaxis and treatment of the teeth and the gums in said bar chamber.

2. A device as defined in claim 1, and further comprising a holding harness with a strap surrounding a user's head and provided with an adjustment element for adjusting a length of said strap so as to hold together upper and lower gums of the user during prefilaxis and treatment.

3. A device as defined in claim 1, wherein said body includes a second such groove formed as an imprint of a portion of a second gum with teeth for receiving the portion of the second gum with teeth of the second gum, said passage means being formed to supply oxygen under high pressure to both said grooves.

4. A device as defined in claim 1, wherein said groove has a plurality of depressions for introducing the teeth individually in said depressions.

5. A device as defined in claim 1, further comprising oxygen supply means communicating with said passage means and including an oxygen line.

6. A device as defined in claim 5, wherein said oxygen line is provided with a pressure relief valve.

7. A device as defined in claim 5, wherein said oxygen line is provided with an oxygen pressure indicating element for indicating an oxygen pressure, and an oxygen pressure regulating element formed as a pressure flow regular for regulating the oxygen pressure in said barochamber in dependence on the indication of the oxygen pressure indicating element.

8. A device as defined in claim 1, and further comprising means for sealing said groove for preventing oxygen loss and increasing an efficiency of oxygen treatment.

9. A device as defined in claim 1, wherein said sealing means include at least one strip attached to an inner surface of said groove.

10. A device for oxygen prophylaxis and treatment, comprising a body which forms a barochamber having at least one groove formed as an actual imprint of teeth of at least one gum of a patient with a portion of the at least one gum, for receiving the teeth of the gum and the portion of the gum in said groove; means for sealing at least one groove so that the teeth of the gum and the portion of the gum are received in said groove in a sealed manner for preventing oxygen loss and increasing efficiency of oxygen treatment; and passage means for supplying oxygen from an oxygen source into said at least one groove so as to provide oxygen prophylaxis and treatment of the teeth and the gums in said barochamber, said sealing means including an O-ring arranged in a lateral depression of said at least one groove.

\* \* \* \* \*